(12) United States Patent
Chen et al.

(10) Patent No.: US 7,378,045 B2
(45) Date of Patent: May 27, 2008

(54) PROCESS FOR THE FORMATION OF HIGH STRENGTH BIO-ABSORBABLE SUTURE FIBERS

(75) Inventors: Gaoyuan Chen, Hillsborough, NJ (US); Dominick Egidio, Flanders, NJ (US)

(73) Assignee: Ethicon, Inc., Somerville, NJ (US)

( * ) Notice: Subject to any disclaimer, the term of this patent is extended or adjusted under 35 U.S.C. 154(b) by 444 days.

(21) Appl. No.: 10/179,480

(22) Filed: Jun. 25, 2002

(65) Prior Publication Data

US 2003/0236554 A1    Dec. 25, 2003

(51) Int. Cl.
- *D01D 5/084* (2006.01)
- *D01D 10/02* (2006.01)
- *D01F 6/16* (2006.01)

(52) U.S. Cl. .............................. 264/211.17; 264/211.22

(58) Field of Classification Search ............... 264/40.6, 264/211.14, 211.17, 211.22

See application file for complete search history.

(56) References Cited

U.S. PATENT DOCUMENTS

| | | | |
|---|---|---|---|
| 5,232,648 A | 8/1993 | Kennedy et al. | |
| 5,288,516 A | 2/1994 | Anderson et al. | |
| 5,425,987 A | 6/1995 | Shawver et al. | |
| 5,571,469 A | * 11/1996 | Suryadevara et al. | .... 264/210.8 |
| 5,585,056 A | 12/1996 | Liu | |
| 5,688,451 A | 11/1997 | Hutton | |
| 6,005,019 A | 12/1999 | Liu | |
| 6,277,927 B1 | 8/2001 | Roby et al. | |

FOREIGN PATENT DOCUMENTS

| | | |
|---|---|---|
| CH | 1195559 A | 10/1998 |
| GB | 1 375 008 A | 11/1974 |
| RU | 2073074 | 9/1997 |
| WO | WO 00 16699 A1 | 3/2000 |

OTHER PUBLICATIONS

Modern Plastics Encyclopedia, p. 476 (1982-1983).*

* cited by examiner

*Primary Examiner*—Leo B. Tentoni

(57) ABSTRACT

A PGA/PLA copolymer suture fiber having a fiber tenacity of between approximately 7.2 to 8.0 grams per denier and a fiber elongation between approximately 22% and 35% is produced by a process that utilizes extruder apparatus having at least one heated zone that is maintained at a temperature of from about 20° C. below the copolymer melting point to about 5° C. above the copolymer melting point, a metering pump and a heated block that are maintained at a temperature of no more than about 40° C. above the copolymer melting point, a spinneret that is maintained at a temperature of from about 40° C. to about 60° C. above the copolymer melting point, and an elongated heated sleeve extending between six and twenty inches from the spinneret that is maintained at a temperature of at least about 60° C. above the copolymer melting point.

15 Claims, 2 Drawing Sheets

PROCESS FOR THE FORMATION OF HIGH STRENGTH BIO-ABSORBABLE SUTURE FIBERS

FIELD OF THE INVENTION

The present invention relates to a device and a process for producing bio-absorbable multifilament sutures having significantly higher tensile strength and higher in vivo break strength retention, while maintaining superior handling characteristics, elongation at break and absorption rate.

BACKGROUND OF THE INVENTION

Biocompatible and bio-absorbable sutures have been widely used for soft tissue approximation for many years. In addition to the requirement of good biocompatibility when implanted in human patients, there are a number of other characteristics that are very important and critical to surgeons and patients. Some of the most important characteristics for a bio-absorbable suture include, but are not limited to, tensile strength, in vivo breaking strength retention, elongation at break, knot tensile strength, in vivo absorption rate and softness.

Various processes, which include melt extrusion and drawing orientation (i.e., spinning and braiding), are currently used to make bio-absorbable multifilament surgical sutures from a copolymer containing glycolide (PGA) and lactide (PLA). Although such processes generally produce PGA/PLA sutures having many of the above-mentioned characteristics within preferred ranges, especially a relatively fast absorption rate (approximately 60-90 days for near complete absorption), they have a relatively low tensile strength compared to nonabsorbable fibers such as nylon or polyester.

Tensile strength is a measure, prior to implantation of the suture braid in a patient, of the amount of tension that a fiber or suture can withstand before it breaks. If the fiber tensile strength is being measured, it is known as the fiber tenacity. The fiber tenacity achieved by processes that produce PGA/PLA sutures is typically in the range of from approximately 6.0 and 6.8 grams per denier (g/d) and sometimes up to 7.2 g/d. Any increase in these tenacity values that could be achieved without diminishing the other characteristics of the suture would be important and useful. In vivo strength retention is a measure of the strength possessed by the suture braid after the suture has been implanted in a patient. Elongation at break is also referred to simply as elongation and is a measure of how much elongation of the suture fibers occurs prior to breakage upon application of tension. It is preferable to maintain the fiber elongation between approximately 22% and 35%.

Various attempts have been made to produce PGA/PLA sutures having a higher tensile strength, while remaining within the preferred ranges for the other desired characteristics, including bio-absorbability and elongation. For example, some suture manufacturers have tried putting more fibers into a braid of a given suture size. Although a higher tensile strength of the overall braid may be obtained in this manner, either the resulting suture would have to be highly oversized or the braid must be tightly packed, which could yield sutures of diminished handling characteristics, such as increased stiffness and poor knot security.

A better way to obtain PGA/PLA sutures having higher tensile strength is to increase the fiber tenacity (measured as force per unit titer), which will yield higher tensile strength for the braid without requiring an increase in the total number of fibers in a braid. For example, U.S. Pat. Nos. 5,585,056 and 6,005,019 disclose the use of plasticizers as a process aid to improve multifilament yarn drawability and the properties of the fibers made from a copolymer having 92.5:7.5 molar ratio poly(glycolide-co-lactide). The plasticizer may have helped to lower the melting point of the copolymer, thereby allowing extrusion without melt fracture at relatively low temperatures. The highest tensile strength obtained by the processes disclosed in these patents was 7.2 grams/denier (g/d), but the elongation at break dropped to 21% and less. This low elongation may lead to severe filament breakage and operational difficulties in the downstream processing of the fibers, including twisting and braiding the fibers together to make a braided suture or other surgical articles. The suture handling characteristics could also be compromised if the fiber elongation at break is too low.

U.S. Pat. No. 6,277,927 discloses that better in vivo strength retention may be achieved by using block copolymers of PGA/PLA to make the suture fibers. However, the fibers spun from such block copolymers failed to exhibit high initial fiber and suture strength. RU 2,073,074 discloses the making of suture fibers by forcing a PGA/PLA copolymer melt to pass through a very thin channel in the spin pack. It was believed that more uniform heating of the fibers could be obtained by the aforesaid method such that better productivity and better fiber properties could be obtained. The maximum fiber tensile strength obtained by the method of RU 2,073,074 for a PGA/PLA copolymer, however, was only about 6.0 to 6.4 g/d. In U.S. Pat. No. 5,288,516, a method is disclosed to make a high tensile strength fiber from PGA, however, sutures made of only PGA fibers have a significantly increased absorption time, which is an undesirable characteristic in many cases where soft tissue approximation is required.

The device and process of the present invention address the shortcomings of the existing apparatus and processes for manufacturing absorbable suture fibers.

As will be described in further detail hereinafter, the present invention introduces modifications to the equipment, temperature profile and heat retention aspects of the known process and equipment.

SUMMARY OF THE INVENTION

The present invention relates to suture fibers made of a glycolide (PGA) and lactide (PLA) copolymer and having a fiber tenacity of between approximately 7.2 to 8.0 grams per denier and a fiber elongation between approximately 22% and 35%.

The process of the present invention produces such high-strength suture fibers and involves using an extruder apparatus having a number of sequentially arranged and interconnected components, each with a temperature control means for maintaining each component at a predetermined temperature. The components of the extruder apparatus include one or more heated zones, a metered pump, a heated block, a spinneret and an elongated heated sleeve extending from the spinneret. Where the extruder apparatus includes one heated zone, the process consists of maintaining the temperature of this heated zone at a temperature from about 20° C. below the copolymer melting point to about 5° C. above the copolymer melting point and maintaining the temperature of the metering pump and the heated block at a temperature of no less than the copolymer melting point and no more than about 40° C. above the copolymer melting point, thereby melting the copolymer as it is pumped through the metering pump and into the heated block. The process further consists of maintaining the spinneret at a temperature from about 40° C. to about 60° C. above the copolymer melting point and forcing the molten copolymer through a plurality of capillary orifices of the spinneret whereby filamentous copolymer fibers are formed.

The heated sleeve is positioned such that the copolymer fibers pass therethrough after formation in the spinneret and the heated sleeve is maintained at a temperature of at least about 60° C. above the copolymer melting point such that the period of time for which the copolymer filaments are substantially above the copolymer melting point is extended.

Where the extruder apparatus includes three heated zones, the first heated zone is maintained at a temperature from about 20° C. below the copolymer melting point to about 5° C. above the copolymer melting point and the second heated zone is maintained at a temperature of at least about equal to the temperature of the first heated zone and no more than about 40° C. above the copolymer melting point. The third heated zone is maintained at a temperature of at least about equal to the temperature of the second heated zone and no more than about 40° C. above the copolymer melting point and the metering pump and the heated block are maintained at a temperature of at least about equal to the temperature of the third heated zone and no more than about 40° C. above the copolymer melting point.

BRIEF DESCRIPTION OF THE DRAWINGS

For a better understanding of the present invention, reference is made to the following detailed description of a preferred embodiment of the present invention considered in conjunction with the accompanying drawings, in which.

DETAILED DESCRIPTION OF THE INVENTION

Figure 1:
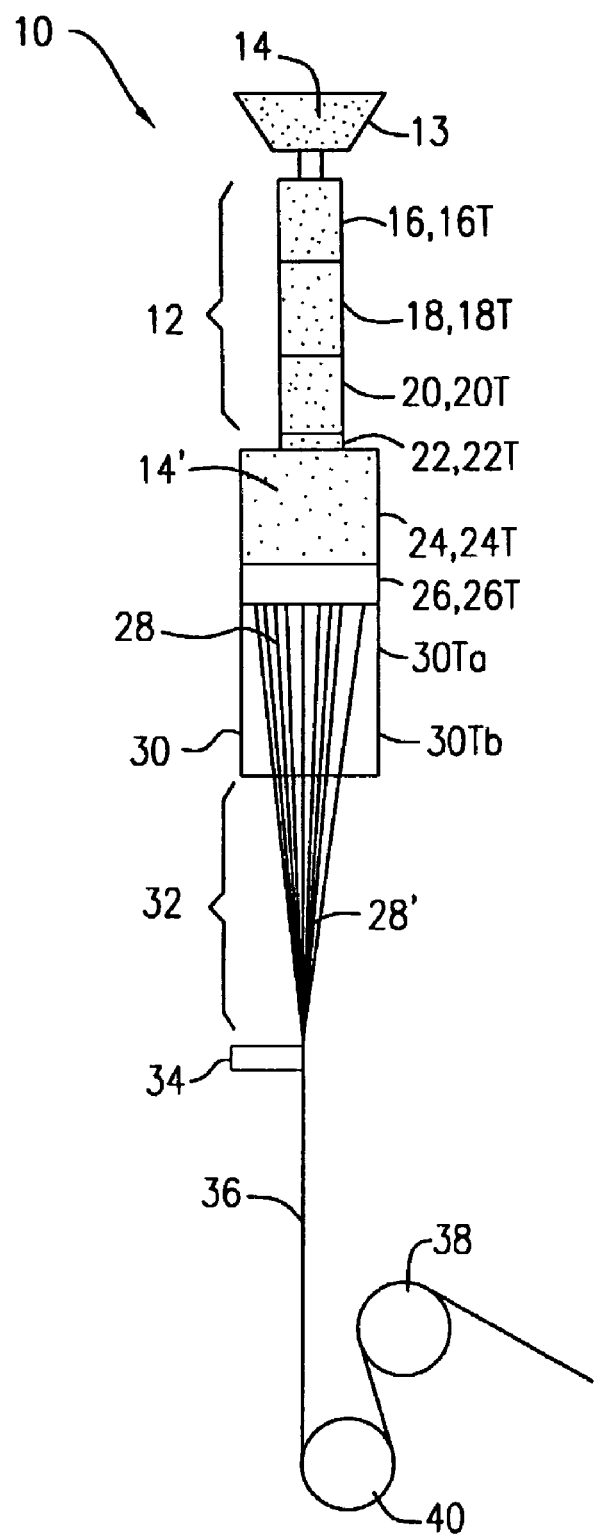
FIG. 1 is a schematic elevational view of the suture production equipment in accordance with the present invention.

FIG. 1 provides a schematic representation of the extruder apparatus 10 that is utilized to perform the process of the present invention for producing bio-absorbable multifilament sutures having increased average tenacity, while maintaining an acceptable range of elongation. More particularly, the extruder apparatus 10 has a number of sequentially arranged interconnected components, including a feeding means, such as hopper 13, and an extruder barrel 12 that is located substantially vertically beneath the hopper 13. The hopper 13 holds and feeds dried copolymer pellets 14 of the type from which the multifilament sutures are to be made into the extruder barrel 12. The copolymer melting point (CMP) of the copolymer pellets 14 is determined by testing a sample of the copolymer pellets 14 with a conventional, standard differential scanning calorimeter (DSC) and selecting the DSC melting peak temperature as the copolymer melting point (CPM).

The extruder barrel 12 includes three sequentially arranged heated zones 16, 18, 20, which are maintained at progressively higher temperatures for melting the copolymer pellets 14 into a copolymer melt 14', as discussed in further detail hereinafter in connection with the process of the present invention. A metering pump 22 is positioned at or near the downstream end of the extruder 12. A heated block 24 is connected to the metering pump 22. The metering pump 22 controls the rate at which the copolymer melt 14' is pumped into the block 24. The extruder barrel 12, and metering pump 22 may be positioned vertically or horizontally adjacent to each other, or in any way suitable for extruding and metering the copolymer flow.

A spinneret 26 is located substantially vertically beneath the block 24 and has a plurality of capillary orifices (not shown). The copolymer melt 14' is pumped through the spinneret 26, under high pressure in the block 24 to form many copolymer filaments 28, as will be described hereinafter. The block 24 may include a series of fine screen filters and breaker plates (not shown) to achieve and maintain a consistency of the copolymer melt 14' that will facilitate pumping the copolymer melt 14' through the spinneret 26.

With continued reference to FIG. 1, a heated sleeve 30 is attached to, and extends substantially vertically beneath, the spinneret 26 for the purpose of maintaining the elevated temperature of the extruded filaments 28, thereby somewhat delaying the quenching of the filaments 28 at the quenching stage 32. A spin finish applicator 34 is positioned after the quenching stage 32 and applies lubricating spin finish (not shown) to the quenched filaments 28', after which the quenched filaments 28' are converged into a bundle 36. The bundled filaments 36 are passed through take-up godet rolls 38, 40, and wound up by a winder (not shown). The said bundled filaments then undergo further processing, including, but not necessarily limited to, drawing and orienting with conventional drawing apparatus (not shown), and, finally, they are braided, to produce the final suture product (not shown).

A distinguishing feature of the aforesaid extruder apparatus 10, compared to equipment used in previously practiced processes for producing multifilament bio-absorbable PGA/PLA sutures, is the inclusion of the heated sleeve 30 having a greater length. The heated sleeve 30 has a length of between approximately six and twenty inches (i.e., approximately 15.2 to 50.8 centimeters (cm)), depending upon the type of copolymer that is used and the yarn total denier (linear density) that is desired. For example, where the copolymer of 80-95 mole percent PGA and 20-5 mole percent PLA is used to produce filament yarn having less than approximately 80 denier (i.e., grams per 9,000 meters or g/9000 m), the heated sleeve 30 of the present invention should be between approximately six and eighteen inches long (i.e., approximately 15.2 to 45.7 cm long), more preferably between eight and sixteen inches long (i.e., approximately 20.3 to 40.6 cm long), and most preferably approximately ten inches long (i.e., approximately 25.4 cm long). For the same copolymer used to produce filaments having approximately 80 denier or greater, the heated sleeve 30 of the present invention should be between approximately ten and twenty inches long (i.e., approximately 25.4 to 50.8 cm long), more preferably between twelve and eighteen inches long (i.e., approximately 30.5 to 45.7 cm long), and most preferably approximately fourteen inches long (i.e., approximately 35.56 cm long). In comparison, where heated sleeves have been used in previously practiced processes, they have been approximately three inches long (i.e., approximately 7.6 cm long) to produce PGA/PLA filament yarn having less than 80 denier and approximately to ten inches long (i.e., approximately 25.4 cm long) to produce PGA/PLA filaments having approximately 80 denier or greater.

It is noted that all of the above-described components of the extruder apparatus 10 shown schematically in FIG. 1 are generally conventional components that are typically known to those having ordinary skill in the art and which are available from commercial sources. More particularly, a suitable extruder barrel 12 and a suitable heated block 24 are available from Davis-Standard, Pawcatuck, Conn. In addition, a suitable metering pump 22 would be available from Zenith Pump Division, Sanford, N.C. Suitable spinnerets 26 and heated sleeves 30 can be obtained from Nissho-Iwai American Corp., New York, N.Y. Similarly, a suitable spin finish applicator 36 could be obtained from Slack & Parr, Inc., Charlotte, N.C. Lastly, it is noted that copolymer pellets 14 suitable for use with the present invention may be obtained from many commercial sources including, but not limited to, META Biomed Co., Ltd., New York, N.Y.

In addition, although not shown, the above-described extruder apparatus 10 must include appropriate heating and temperature control devices. As will be obvious to one of ordinary skill in the art, heating devices are required to heat each of the various above-described heated components to the desired temperatures (which will be discussed in detail hereinafter). The temperature control devices are necessary to detect and maintain the temperatures of the components within the predetermined desired ranges in accordance with the present invention (which will be discussed in detail hereinafter). Such heating and temperature control devices are also well-known and readily available from commercial sources, including, but not limited to, Honeywell Inc., Fort Washington, Pa.

With continued reference to FIG. 1, the process of the present invention, which includes the two basic steps of melt extrusion and drawing orientation, will now be described in detail as it is performed utilizing the above-described extruder apparatus 10. During the melt extrusion step, dried copolymer pellets 14 are fed from the hopper 13, into the extruder barrel 12 and heated by the heated zones 16, 18, 20 of the extruder barrel 12 into a copolymer melt 14' that is then pumped into the heated block 24 by the metering pump 22. The copolymer melt 14' is then further pumped, under high pressure in the block 24, through multiple orifices (not shown) of the spinneret 26, thereby forming a plurality of extruded filaments 28. As many as 40 or more filaments 30 at a time may be produced in this manner. As the filaments 28 emerge from the spinneret 26 they are surrounded by the heated sleeve 30 which maintains the elevated temperature of the freshly extruded filaments 28. The filaments 28 are then quenched and solidified before the lubricating spin finish is applied by the spin finish applicator 34. Thereafter, the filaments are gathered into a bundle 36, passed through godet rolls 38, 40, drawn, oriented and braided.

The process of the present invention includes operation of the above-described extruder apparatus 10 such that a particular temperature profile is created from the heated zones 16, 18, 20 of the extruder barrel 12, to the spinneret 26, to the temperature of the heated sleeve 30, as will be discussed hereinafter. To facilitate discussion and illustration of the aforesaid temperature profile, the temperature of each of the heated components of the extruder apparatus 10 will hereinafter be referred to by using a temperature label composed of its reference number and the letter "T" thereafter. For example, the temperature of the first heated zone 16 of the extruder barrel 12 will be referred to hereinafter using the temperature label 16T and the temperature of the spinneret 26 will be referred to hereinafter using the temperature label 26T. Moreover, it is noted that the heated sleeve 30 may have two temperature zones, which will be referred to hereinafter using the temperature labels 30Ta and 30Tb, respectively (see FIG. 1). The temperature labels are noted, for reference, in FIG. 1.

Further more, it is noted that suitable temperatures for the heated components of the extruder apparatus 10 will depend upon the melting temperature of the type of copolymer pellets 14 that are used. Therefore, suitable temperatures for the heated components of the extruder apparatus 10 will be discussed in terms relative to the melting point of the copolymer pellets 14.

With reference still, initially, to FIG. 1, a typical temperature profile in accordance with the present invention includes keeping the temperature 16T of the first heated zone 16 of the extruder barrel 12 as low as possible, preferably not less than approximately 20 C. below the melting point of the copolymer pellets 14 and no more than 5° C. above the melting point of the copolymer pellets 14 (hereinafter referred to as the "copolymer melting point" or "CMP"). Most preferably, the temperature 16T of the first heated zone 16 of the extruder barrel 12 should be approximately 15° C. to 18° C. below the CMP. The temperatures in subsequent zones, including the second and third heated zones 18, 20 of the extruder barrel 12, the metering pump 22 and the block 24, should be gradually and slightly increased, but each temperature 18T, 20T, 22T, 24T should be no more than 40° C. above the CMP. More preferably, the temperatures 18T, 20T, 22T, 24T of these subsequent zones should each be no more than 25° C. above the CMP.

The temperature 26T of the spinneret 26 should be between 20° C. and 40° C. above the block 24 temperature and between 40-60° C. above the CMP such that, when the copolymer melt 14' is about to enter the capillaries of the spinneret 26, the copolymer melt 14' is rapidly heated. The temperature within the heated sleeve 30 should each be at least 60° C. above the CMP, whereby, after the copolymer melt 14' is extruded through the spinneret 26, the freshly extruded filaments 28 will be maintained in a hot environment for the entire length of the heated sleeve 30. As discussed hereinabove, the length of the heated sleeve 30 is between approximately six and twenty inches (i.e., approximately 15.2 to 50.8 cm), depending upon the type of copolymer that is used and the yarn denier (linear density) that is desired. Furthermore, while the heated sleeve 30 does not have to include multiple temperature zones, where two or more zones do exist, the temperature difference between two vertically adjacent zones (i.e., characterized by temperatures 30Ta and 30Tb) should not be more than about 30° C. apart and the temperature 30Ta of the zone closer to the spinneret 26 should be greater than the temperature 30Tb of the zone that is more remote from the spinneret 26. After the filaments 28 pass through and emerge from the heated sleeve 30, they are quenched by ambient air, or any known suitable quench medium, and undergo the further processing steps described previously hereinabove.

Figure 2:
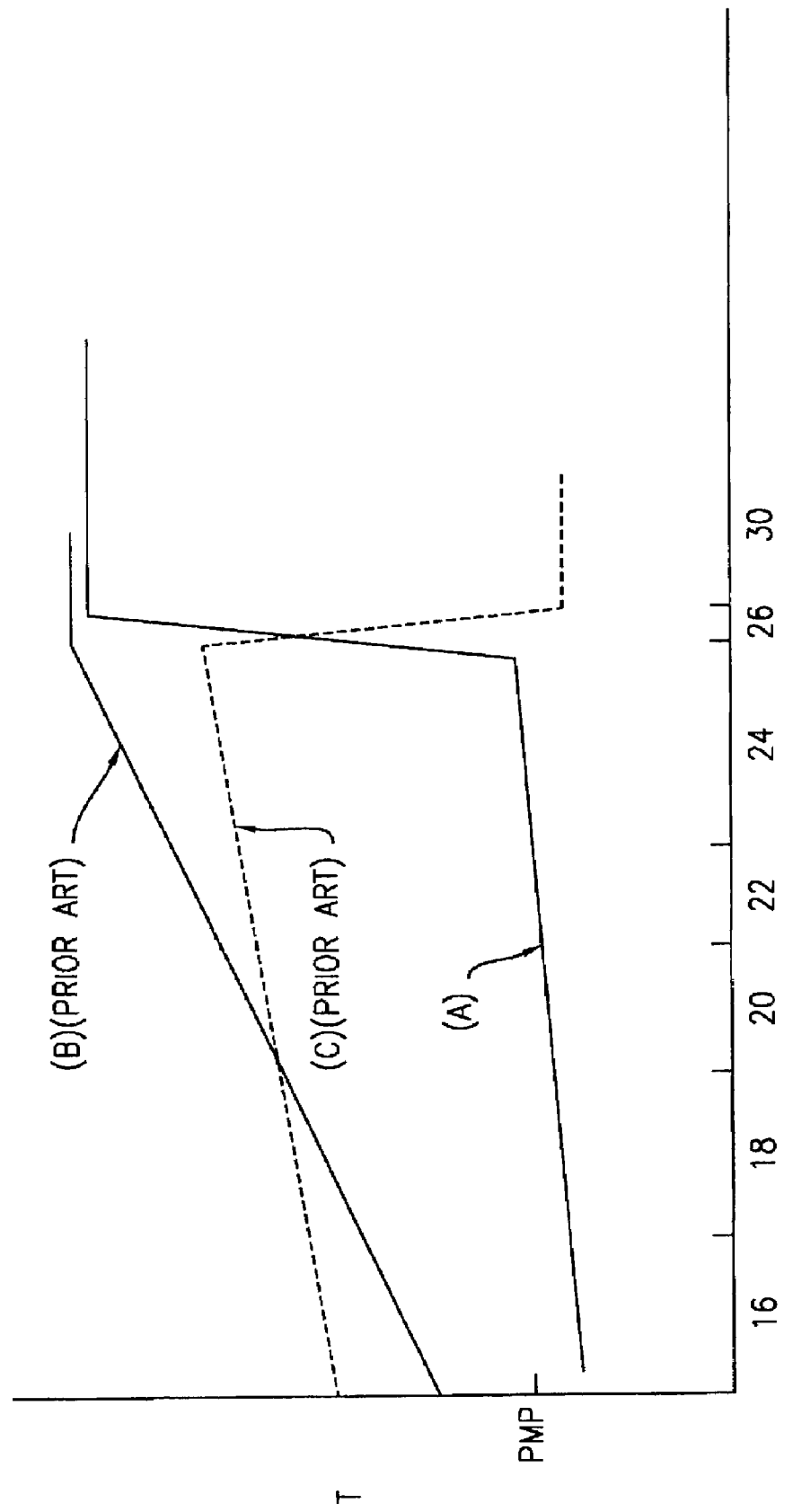
FIG. 2 is a chart showing the temperature profiles of the process of the present invention and certain prior art process.

FIG. 2 provides a comparative representation of the typical temperature profiles of the process of the present invention (A), the existing process currently performed to produce 90 mole %/10 mole % PGA/PLA suture filaments, of which the present invention is an improvement (B), and the processes disclosed in certain prior art patents (C). More particularly, as can be seen in FIG. 2, the typical temperature profile of the process of the present invention (A) begins a few degrees below the CMP (at the first heated zone 16 of the extruder barrel 12). In contrast, the temperature profiles of the existing process (B) and the prior art process (C) each begin significantly above the CMP. Furthermore, the temperature profile of the process of the present invention (A) rises only gradually to approximately 25° C. to 40° C. above the CMP in the heated block 24, just prior to the spinneret 26. The temperature profile of the existing process (B) rises to be greater than 40° C. above the CMP in the heated block 24. Although the temperature profile of the prior art processes (C) rises gradually, like the profile of the present invention (A), it does not typically rise as high as either of the other two profiles (A), (B).

FIG. 2 shows that the temperature profile of the process of the present invention (A) rises drastically at the spinneret 26, whereas neither of the other profiles (B), (C) show any sudden increase of temperature at the spinneret 26. In fact, the temperature profile of the existing process (B) is approaching the highest temperature just prior to the spinneret 26. In addition, the profiles (A), (B), (C) in FIG. 2 show that, while the temperature attained in the spinneret 26 in the process of the present invention is maintained for a substantial length after the filaments 28 leave the spinneret 26, the temperature attained in the spinnerets in the existing process (B) is maintained for a shorter distance after the filaments leave the spinnerets. Furthermore, the temperature profile of the prior art processes (C) generally decreases significantly to a lower temperature immediately after the filaments leaving the spinneret 26.

The result of utilizing the above-described process, which creates the above-discussed temperature profile (A), is the production of PGA/PLA suture fibers that can be drawn into multifilament yarn of 20 to 100 denier, containing about 80 to 90 mole percent PGA and about 5 to 20 mole percent PLA. Moreover, surprisingly, this multifilament yarn product has a unique combination of an average tenacity of at least 7.2 g/d (which is significantly improved over the existing and prior art processes) and an elongation in the range of approximately 22% to 35% (which is well within the acceptable range for bio-absorbable sutures). Both the fiber tenacity and the elongation of the yarn were measured using a Statimat testing machine (either Model M or Model ME available from Textechno Herbert Stein GmbH & Co., KG of Monchengladback, Germany), with a gauge length of 500 millimeters (mm) and a strain rate of 720 mm per minute. In addition, the sutures made from this higher tenacity multifilament yarn has a significantly higher out-of-package tensile strength, higher in vitro and in vivo breaking strengths and higher % breaking strength retention (% BSR) (i.e., % BSR at 21 or 28 days), than the sutures made from yarns produced by the existing or prior art processes.

The process of the present invention is particularly suitable for the production of filaments from a copolymer of about 90 mole percent PGA and about 10 mole percent PLA, which has a CMP of about 200° C., as determined by standard DSC method. In such a preferred application of the process of the present invention, the temperature profile should include an initial temperature T16 at the first heated zone 16 of 205° C. or less.

The temperatures in subsequent zones, including the second and third heated zones 18, 20 of the extruder barrel 12, the metering pump 22 and the block 24, should be gradually and slightly increased, each temperature 18T, 20T, 22T, 24T being no more than 240° C. and, preferably, no more than 230° C. The temperature 26T of the spinneret 26 should be at least 240° C. and, in any event, should also be at least 20° C. higher than the temperature of the pump 22 and the heated block 24. Preferably, the temperature 26T of the spinneret 26 should be in the range of about 245° C. to 265° C.

EXAMPLES

Eight examples of the process of the present invention and four comparative examples of the existing process (discussed hereinabove) were performed and are discussed hereinafter.

Initially, it is noted that for all twelve of the examples, a copolymer of about 90 mole percent PGA and about 10 mole percent PLA, which has a CMP of about 200° C. was used to produce filaments and, thereafter, bio-absorbable multifilament sutures. The CMP was determined by the above-discussed standard DSC method at a heating rate of 20° C. per minute in nitrogen and using a sample of about 5-10 milligrams in size, In addition, except for the heated sleeves 30 and the various temperatures 16T, 18T, 20T, 22T, 24T, 26T, 30Ta, 30Tb, the extruder apparatus 10 and the process conditions were substantially the same for all twelve examples. For example, the spinneret 26 had capillaries of 0.305 millimeters in diameter and an L/D ratio of 7:1.

The take up speed for the as-spun filaments was fixed at 528 meters per minute. Except for one of the examples of the process of the present invention (i.e., Example No. 2), the drawing conditions for the remaining eleven examples consisted of a feed roll speed of about 200 feet per minute, a draw roll speed of about 998 feet per minute and a let-off roll speed of about 1,000 feet per minute. Example 2 was drawn at the same draw ratio except that the speed was slower (half of the other samples), which made no difference on the fiber properties. The feed roll temperatures for all twelve examples ranged between about 80° C. and 88° C. and the draw roll temperatures ranged between about 90° C. and 100° C.

With reference to the length of the heated sleeve 30, it is noted that the heated sleeve 30 used to perform each of the examples for the existing process (Example Nos. 9C-12C) was approximately three inches long (i.e., approximately 7.6 cm long) with only one temperature zone. The heated sleeve 30 used to perform seven of the eight examples for the present invention (Example Nos. 1-7) was approximately ten inches long (i.e., approximately 25.4 cm long) and the heated sleeve 30 used for Example No. 8 was approximately fourteen inches long (i.e., approximately 35.5 cm long).

The following Table 1 provides the temperatures 16T, 18T, 20T, 22T, 24T, 26T, 30Ta, 30Tb, for the eight examples of the process of the present invention (i.e., Example Nos. 1-8), as well as the temperatures 16T, 18T, 20T, 22T, 24T, 26T, 30Ta, for the four comparative examples of the existing process (Example Nos 9C-12C).

TABLE 1

Temperatures During Extrusion

| Example No. | Target Yarn Denier (g/9000 m) | 16T (° C.) | 18T (° C.) | 20T (° C.) | 22T (° C.) | 24T (° C.) | 26T (° C.) | 30Ta (° C.) | 30Tb (° C.) |
|---|---|---|---|---|---|---|---|---|---|
| 1 | 28 | 182 | 196 | 199 | 218 | 218 | 260 | 288 | 288 |
| 2 | 28 | 193 | 213 | 221 | 235 | 238 | 260 | 274 | 274 |
| 3 | 56 | 182 | 196 | 199 | 218 | 218 | 260 | 288 | 288 |
| 4 | 56 | 182 | 194 | 199 | 218 | 218 | 254 | 293 | 277 |
| 5 | 56 | 193 | 213 | 221 | 232 | 235 | 257 | 279 | 279 |

TABLE 1-continued

Temperatures During Extrusion

| Example No. | Target Yarn Denier (g/9000 m) | 16T (° C.) | 18T (° C.) | 20T (° C.) | 22T (° C.) | 24T (° C.) | 26T (° C.) | 30Ta (° C.) | 30Tb (° C.) |
|---|---|---|---|---|---|---|---|---|---|
| 6 | 56 | 182 | 195 | 199 | 216 | 216 | 252 | 293 | 277 |
| 7 | 56 | 200 | 206 | 210 | 216 | 216 | 243 | 292 | 292 |
| 8 | 80 | 198 | 212 | 213 | 227 | 227 | 249 | 293 | 277 |
| 9C | 56 | 182 | 196 | 199 | 218 | 218 | 266 | 277 | n/a |
| 10C | 56 | 204 | 221 | 229 | 238 | 246 | 274 | 291 | n/a |
| 11C | 80 | 204 | 221 | 229 | 254 | 260 | 279 | 291 | n/a |
| 12C | 80 | 199 | 221 | 229 | 252 | 254 | 271 | 288 | n/a |

With reference to Table 1, it is noted that in each of Example Nos. 1-8 for the process of the present invention, the temperature profile represented by the data therein conforms generally to the typical temperature profile for the process of the present invention (A) shown in FIG. 2. More particularly, the temperature profiles for each of Examples 1-8 begins at or below the CMP (i.e., at 200° C. or less) and rises gradually, until reaching a temperature 24T at the heated block 24 that is not more than 40° C. above the CMP (i.e., is not more than 240° C.), at which point it rises quickly in the spinneret 26 where the temperature T26 is at least 240° C. and, in each case, is more that 20° C. above the temperature 24T of the block 24. Similarly, it is noted that in each of comparative Example Nos. 9C-12C for the existing process, the temperature profile represented by the data therein conforms generally to the typical temperature profile for the existing process (B) shown in FIG. 2.

The following Table 2 provides the data for the characteristics of the resulting multifilament yarns for each of the twelve examples, including the number of filaments, the tenacity, the elongation, and the toughness.

TABLE 2

Characteristics of Drawn Yarn

| Example No. | Type | No. of Filaments | Yarn Denier | Tenacity (g/d) | Elongation (%) | Toughness (g-cm/d) |
|---|---|---|---|---|---|---|
| 1 | Natural | 14 | 28.0 | 7.5 | 26.2 | 54 |
| 2 | Dyed | 14 | 28.9 | 7.3 | 25.8 | 51 |
| 3 | Natural | 26 | 56.3 | 7.5 | 26.1 | 53 |
| 4 | Natural | 26 | 56.4 | 7.9 | 23.5 | 51 |
| 5 | Dyed | 28 | 57.3 | 7.4 | 25.6 | 49 |
| 6 | Dyed | 28 | 56.2 | 7.9 | 25.2 | 54 |
| 7 | Dyed | 28 | 56.0 | 7.6 | 23.2 | 49 |
| 8 | Natural | 40 | 80.3 | 7.5 | 25.5 | 50 |
| 9C | Natural | 28 | 56.3 | 6.4 | 26.1 | 48 |
| 10C | Dyed | 28 | 56.1 | 6.4 | 25.1 | 41 |
| 11C | Natural | 40 | 78.9 | 6.5 | 23.1 | 39 |
| 12C | Dyed | 40 |  | 6.4 | 23.2 | 38 |

With reference to Table 2, it is noted that the process of the present invention (i.e., Example Nos. 1-8) resulted in the production of multifilament yarns which surprisingly had a significantly improved fiber tenacity in the range of about 7.2 g/d to about 7.9 g/d, compared to the existing process (i.e., fiber tenacity of about 6.4-6.5 g/d), while maintaining an elongation in the range of about 23% to about 26% (substantially the same range as for Examples 9C-12C of the existing process). Yarn tensile properties, including fiber tenacity and elongation were measured using the above-discussed Statimat testing machine (a Model M and a Model ME Statimat were both used in connection with these examples), with a gauge length of 500 mm and a strain rate of 720 mm per minute. In particular, the toughness was determined by calculating the area under the stress-strain curve, measured in units of gram-centimeters per denier (g-cm/d).

In addition, braided sutures of USP size 5/0-1 were prepared using the multifilament yarns resulting from Example Nos. 1-8 and these sutures showed an average of 12% higher initial straight tensile strength and 11% higher knot strength than the control samples using the same amounts of materials. Furthermore, the in vivo breaking strength retentions at 21 and 28 days, respectively, were about 5-10% higher than the control produced using the existing process. The sutures made using the process of the present invention had excellent handling characteristics and were essentially entirely absorbed in vivo within about 70 days.

While it is known that higher process temperatures tend to lead to thermal degradation of the polymer and, therefore, leads to the production of filaments having diminished characteristics, including fiber tenacity, elongation and in vivo breaking strength, it was previously believed that the process temperatures had to be significantly above the melting point of the polymer during the majority of the extrusion step of the manufacturing process (see, e.g., FIG. 2, temperature profiles (B) and (C)) to ensure proper extrusion. It has, however, been discovered in connection with the present invention that it is advantageous to begin with a temperature that is near or a bit below the melting point of the polymer (in the first heated zone 16) and to extend the period of time at the end of the extrusion step that the filaments are exposed to temperatures that are significantly higher than the melting point (in the spinneret 26 and elongated heated sleeve 30). This temperature profile is achieved by gradually raising the temperature within the extrusion barrel 12, the pump 22 and the block 24 up to, but not higher than about 40° C. above the melting point of the polymer, and then quickly raising the temperature up to about at least about 40° C. above the melting point in the spinneret region 26 and at least 60° C. above the melting point in the heated sleeve 30.

It will be understood that the embodiments described herein are merely exemplary and that a person skilled in the art may make many variations and modifications, including but not limited to those discussed hereinabove, without departing from the spirit and scope of the present invention. All such variations and modifications are intended to be included within the scope of the invention as defined in the appended claims.

We claim:

1. A process for producing suture fibers made of a glycolide and lactide copolymer in an extruder apparatus having a plurality of sequentially arranged and interconnected components including an extruder having at least one heated zone, a metering pump, a heated block, a spinneret having a plurality of capillary orifices and being located substantially vertically beneath the heated block, and a heated sleeve located substantially beneath the spinneret, a temperature control means being provided for each component for maintaining each component at a predetermined temperature, said process comprising the sequential steps of:

feeding the copolymer having a copolymer melting point, defined as the DSC peak melting temperature thereof, to the extruder;

maintaining the at least one heated zone of the extruder at a temperature of from about 20° C. below the copolymer melting point to about 5° C. above the copolymer melting point;

maintaining the metering pump and the heated block at a temperature of no less than the copolymer melting point and no more than about 40° C. above the copolymer melting point, wherein the temperature of the metering pump and the heated block is greater than the temperature of the at least one heated zone of the extruder;

maintaining the spinneret at a temperature from about 40° C. to about 60° C. above the copolymer melting point, wherein the temperature of the spinneret is greater than the temperature of the metering pump and the heated block;

activating the metering pump to transfer the copolymer from the extruder to the heated block, whereupon the copolymer is substantially melted;

forcing the substantially molten copolymer through the plurality of capillary orifices of the spinneret whereby filamentous copolymer fibers are formed; and maintaining the heated sleeve at a temperature of at least 60° C. above the copolymer melting point such that the period of time for which the copolymer fibers are substantially above the copolymer melting point is extended, the heated sleeve being positioned such that the copolymer filaments pass through the heated sleeve after formation in the spinneret, and the heated sleeve being between approximately six and eighteen inches long, the copolymer filaments having a denier per filament of about 2.0.

2. The process according to claim 1, wherein the heated sleeve is approximately ten inches long.

3. The process according to claim 1, wherein the heated sleeve is approximately fourteen inches long.

4. The process according to claim 1, wherein the extruder includes three heated zones, said process further including the steps of:

maintaining the second heated zone at a temperature of at least about equal to the temperature of the first heated zone and no more than about 40° C. above the copolymer melting point;

maintaining the third heated zone at a temperature of at least about equal to the temperature of the second heated zone and no more than about 40° C. above the copolymer melting point; and maintaining the metering pump and the heated block at a temperature of at least about equal to the temperature of the third heated zone and no more than about 40° C. above the copolymer melting point.

5. The process according to claim 4, wherein the first heated zone is maintained at a temperature of from about 15 to 18° C. below the copolymer melting point to no more than about 5° C. above the copolymer melting point.

6. The process according to claim 4, wherein the second and third heated zones, the metering pump and the heated block are each maintained at a temperature of no more than about 25° C. above the copolymer melting point.

7. The process according to claim 4, wherein the spinneret is maintained at a temperature of from about 20° C. to 40° C. above the temperature of the metering pump and heated block.

8. The process according to claim 4, wherein the heated sleeve includes a first heated zone proximate to the spinneret and a second heated zone remote from the spinneret, each of which are maintained at temperatures that are not more than about 30° C. apart, and the temperature of the heated zone proximate to the spinneret is greater than the temperature of the heated zone remote from the spinneret.

9. The process according to claim 1, wherein the copolymer comprises between approximately 80 to 95 mole percent of glycolide and between approximately 5 to 20 mole percent of lactide, to a total of 100 mole percent, and has a copolymer melting point of about 200° C.

10. The process according to claim 9, wherein the copolymer comprises between approximately 85 to 95 mole percent of glycolide and between approximately 5 to 15 mole percent of lactide, to a total of 100 mole percent.

11. The process according to claim 4, wherein the copolymer comprises between approximately 80 to 95 mole percent of glycolide and between approximately 5 to 20 mole percent of lactide, to a total of 100 mole percent, and has a copolymer melting point of approximately 200° C.

12. The process according to claim 11, wherein the spinneret is maintained at a temperature of at least about 240° C. and at least about 20° C. above the temperature of the metering pump and heated block.

13. The process according to claim 12, wherein the spinneret is maintained at a temperature from about 245° C. and 265° C.

14. The process according to claim 13, wherein
the first heated zone is maintained at a temperature of from about 180° C. to 205° C.;
the second heated zone is maintained at a temperature of at least about equal to the temperature of the first heated zone and no more than about 240° C.;
the third heated zone is maintained at a temperature at least about equal to the temperature of the second heated zone and no more than about 240° C.; and
the metering pump and the heated block are each maintained at a temperature at least about equal to the temperature of the third heated zone and no more than about 240° C.

15. The process according to claim 14, wherein the heated sleeve is maintained at a temperature of at least about 60° C. above the copolymer melting point.

* * * * *